(12) United States Patent
Ein-Gal

(10) Patent No.: US 8,270,569 B2
(45) Date of Patent: Sep. 18, 2012

(54) CASCADED MODULATION SYSTEM

(76) Inventor: Moshe Ein-Gal, Ramat Hasharon (IL)

( * ) Notice: Subject to any disclaimer, the term of this patent is extended or adjusted under 35 U.S.C. 154(b) by 253 days.

(21) Appl. No.: 12/833,986

(22) Filed: Jul. 11, 2010

(65) Prior Publication Data
US 2012/0008743 A1    Jan. 12, 2012

(51) Int. Cl.
*A61N 5/10* (2006.01)

(52) U.S. Cl. .......................................... 378/65; 378/157
(58) Field of Classification Search .................. 378/145, 378/146, 148, 150, 157, 158, 64, 65, 84, 378/85
See application file for complete search history.

(56) References Cited

U.S. PATENT DOCUMENTS

| | | | |
|---|---|---|---|
| 6,043,890 A * | 3/2000 | Spink et al. | 356/614 |
| 6,307,918 B1 * | 10/2001 | Toth et al. | 378/158 |
| 2009/0022274 A1 * | 1/2009 | Gertner et al. | 378/65 |

* cited by examiner

*Primary Examiner* — Hoon Song
(74) *Attorney, Agent, or Firm* — Dekel Patent Ltd.; David Klein

(57) ABSTRACT

A modulation system for modulating a radiation beam, including a plurality of cascaded modulators, a positioner operable to change positions of each of the modulators between in-beam and out-of-beam positions, wherein in the in-beam position the modulator is in a path of a radiation beam for at least a majority of a total cross-section of the beam and in the out-beam position the modulator is not in the path of the radiation beam, and a processor in communication with a beam modifier and with the positioner operative to determine operating times or motion speed for changing the respective positions of the modulators between the in-beam and out-of-beam positions, wherein the beam modifier is operable to change during irradiation an aperture of the radiation beam and the positioner is operative to change during irradiation a relative position of the target and the radiation beam.

13 Claims, 4 Drawing Sheets

CASCADED MODULATION SYSTEM

FIELD OF THE INVENTION

The present invention generally relates to a system and method for radiation therapy or diagnostics with beam modulation, such as but not limited to, intensity modulated radiation therapy (IMRT) or diagnostics, and particularly to dynamic beam attenuators for such therapy or diagnostics, wherein the relative position of a radiation source and an irradiated target vary during irradiation.

BACKGROUND OF THE INVENTION

The intensity of the radiation beam used for radiotherapy is required to be time-invariant in some applications or modulated according to beam orientation in other applications, such as Intensity Modulated Radiation Therapy (IMRT).

In IMRT, the delivery can be done using compensators, i.e., filters individually made for each projection, that reduce the intensity to a predefined level in each part of the field due to attenuation of the primary photon beam. However, when using several projections, each projection requiring individual compensators, this technique is time-consuming and requires a lot of effort. The most common way to deliver IMRT is by the use of a multi-leaf collimator (MLC) that has collimator leaves that can be individually positioned to block a small part of the field and thereby shape the beam in the lateral direction into various irregular shapes. In each projection, the collimator leaves are moved during the treatment and thereby various parts of the cross-section of the beam are irradiated during various times, i.e., the dose distribution is modulated.

Currently available IMRT delivery techniques include fixed beam angle delivery and intensity modulated arc therapy (IMAT). When radiation is delivered with fixed beam angles, a series of beam shapes are delivered at each beam angle either dynamically, wherein the leaves of the MLC move during irradiation, or in a step-and-shoot fashion, where the radiation is paused during the movement of MLC leaves. In contrast, IMAT uses multiple overlapping arcs of radiation in order to produce intensity modulation.

While high spatial-frequency modulation can be achieved by individually manufactured physical compensators, low frequency modulation is achieved with standard wedges. A wedge is a device commonly used in radiation therapy to shape the dose distribution from external photon beams. It is available on the radiation therapy machines of all major manufacturers. The most basic form of wedge is the physical wedge, made of metals such as lead or stainless steel. An external physical wedge is mounted outside the machine head. A set of standard wedge angles, typically 15°, 30°, 45°, and 60° are exchangeable. A single internal wedge of 60°, called the 'universal' wedge, is also used: the wedge is mounted inside the machine head and wedge angles less than 60° are obtained by combining a 60° wedge field and an open field with weights determined by the desired wedge angle. For example, a 30° equivalent wedge is obtained by irradiating half the time with the 60° wedge and half the time with an open field. Since positioning the wedge in place is slow, the beam is turned off during the wedge motion. The movements of a wedge into in-beam position and subsequently into out-of-beam position are in opposite directions. While the wedge functions properly when stationary, un-compensated radiation would be delivered if radiation is applied during wedge motion.

SUMMARY OF THE INVENTION

The present invention seeks to provide improved dynamic beam modulators (attenuators) for therapy or diagnostics, wherein changing the positions of the modulators between in-beam and out-of-beam positions may be executed during irradiation, as is described more in detail hereinbelow. In accordance with embodiments of the invention, modulators arranged in cascade can be quickly inserted during radiation into the beam path and withdrawn out of the path, wherein the insertion and withdrawal are done at respective time increments and the modulators remain in the beam path for a certain length of time. The modulators may be short or small, about target size. Degrees of modulation are determined by the length of the time a modulator stays in the beam path, rather than by modulator continuous position There is thus provided in accordance with an embodiment of the present invention a modulation system for modulating a radiation beam, including a plurality of cascaded modulators, a positioner operable to change positions of each of the modulators between in-beam and out-of-beam positions, wherein in the in-beam position the modulator is in a path of a radiation beam for at least a majority of a total cross-section of the beam and in the out-beam position the modulator is not in the path of the radiation beam, and a processor in communication with a beam modifier and with the positioner operative to determine operating times or motion speed for changing the respective positions of the modulators between the in-beam and out-of-beam positions, wherein the beam modifier is operable to change during irradiation an aperture of the radiation beam and the positioner is operative to change during irradiation a relative position of the target and the radiation beam.

In accordance with an embodiment of the present invention the positioner is operable to change the position of a modulator in less than 100 msec.

In accordance with an embodiment of the present invention the modulators are configured such that their respective modulation patterns do not vary with respect to at least one spatial coordinate.

In accordance with an embodiment of the present invention the positioner is operable to move the modulators to in-beam positions and subsequently to out-of-beam positions in the same respective direction.

In accordance with an embodiment of the present invention the modulation system includes cascaded modulators such that the combined modulation pattern of the cascaded modulators is generally uniform and the maximum thickness of the combined cascaded modulators is substantially equal to that of each modulator.

In accordance with an embodiment of the present invention the modulation system includes cascaded modulators configured such that their respective modulation patterns or their respectively associated modulated beam intensities vary generally as polynomials of order N, wherein N is one of 0, 1, 2, etc.

In accordance with an embodiment of the present invention the cascaded modulators are configured such that their respective modulation patterns are rotated about the beam direction with respect to each other.

In accordance with an embodiment of the present invention the modulation system includes a group of N+1 cascaded modulators rotated with respect to each other about the beam direction, wherein the N+1 cascaded modulators are configured such that their respective modulation patterns or their respectively associated modulated beam intensities vary generally as a polynomial of order N, wherein N is one of 0, 1, 2, etc.

In accordance with an embodiment of the present invention the modulation system is part of a radiotherapy system that includes a radiation source operable to produce a radiation beam towards a target, a collimator and an orientation changer operable to change a relative position of the radiation source with respect to the target.

There is also provided in accordance with an embodiment of the present invention a method for performing radiotherapy including providing a modulation system including cascaded modulators, producing a radiation beam from a radiation source toward a target, and inserting combinations of cascaded modulators in the path of the radiation beam for corresponding time intervals.

In accordance with an embodiment of the present invention the method includes relating the corresponding time intervals to outputs of at least one of a timer, a radiation sensor and the orientation changer.

In accordance with an embodiment of the present invention the method includes continuously irradiating the target over an irradiation time with the radiation beam modulated by the modulation system, wherein the relative position of the radiation source with respect to the target during irradiation may be fixed or changing.

BRIEF DESCRIPTION OF THE DRAWINGS

The present invention will be understood and appreciated more fully from the following detailed description, taken in conjunction with the drawings in which.

DETAILED DESCRIPTION OF EMBODIMENTS

Figure 1:
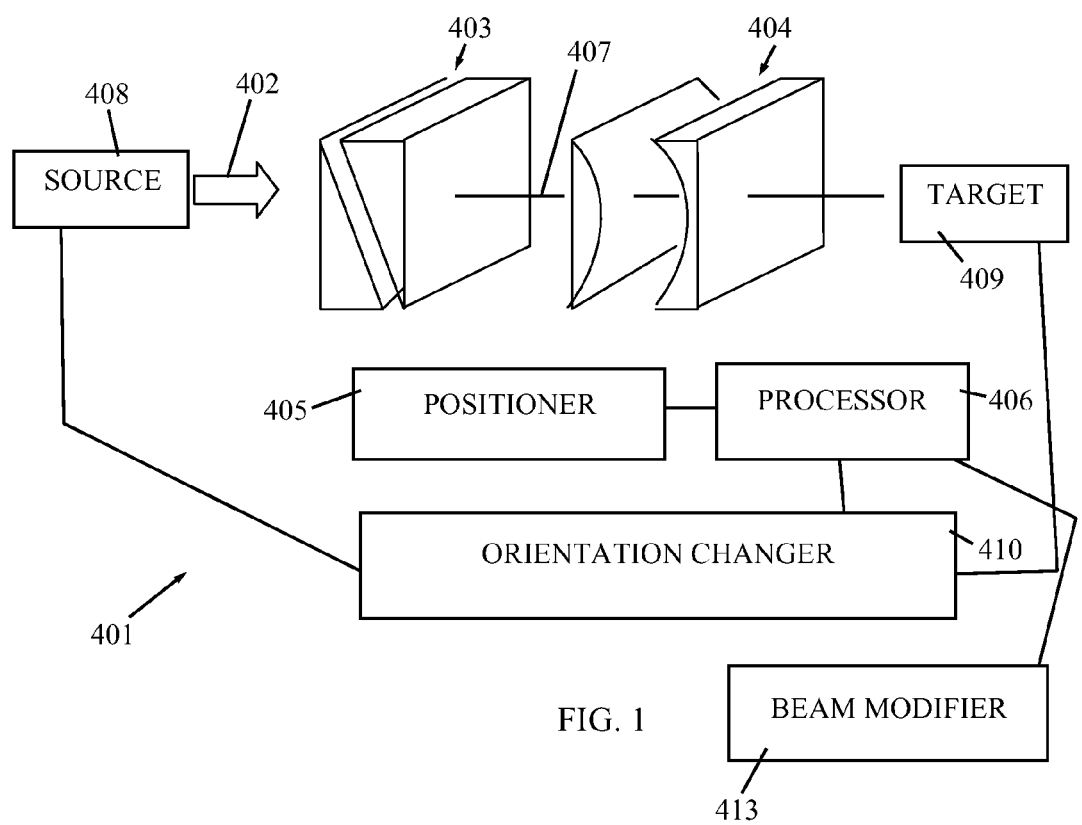
FIG. 1 is a simplified illustration of a modulation system for modulating a radiation beam, constructed and operative in accordance with an embodiment of the present invention.

Reference is now made to FIG. 1, which illustrates a modulation system 401 for modulating a radiation beam 402, constructed and operative in accordance with an embodiment of the present invention.

The modulation system 401 includes a first modulating cascaded group 403 and a second modulating cascaded group 404 both placeable in a path of radiation beam 402 for modulation thereof. There can be any number of modulating cascaded groups used in system 401, and together they form a modulation cascade. The modulating cascaded groups are aligned along a modulating system axis 407, which may be collinear with the path of the radiation beam 402.

Each modulating cascaded group includes a plurality of modulating (attenuating) elements that form a modulation cascade, as described in the embodiments above. Each modulating cascaded group defines a modulation pattern. For example, first modulating cascaded group 403 includes two or more triangular wedges. Second modulating cascaded group 404 includes two or more concave/convex elements. In accordance with an embodiment of the invention, the modulating elements of groups 403 and 404 have dimensions generally limited to the beam cross-section. The modulating (attenuating) elements can be moved together or individually in any linear or rotational direction. The modulating (attenuating) elements may be made of known attenuating materials, such as but not limited to, tungsten.

A positioner 405 (e.g., step motor, linear actuator, etc.) is operative to insert one or more of the modulators of a modulating cascaded groups in the path of radiation beam 402 for a required sequence of modulation time intervals. A processor 406 is operative to determine the required sequence of modulation time intervals and communicates with positioner 405 to control the operation of positioner 405.

The plurality of modulating cascaded groups 403 and 404 can be configured such that a combination of their modulation patterns does not vary with respect to at least one spatial coordinate, or alternatively varies linearly with respect to at least one coordinate, or alternatively varies along a direction perpendicular to the path of radiation beam 402, or in any other manner. Additionally or alternatively, the modulators in each of the modulating cascaded groups can be rotated with respect to each other about modulating system axis 407. For example, the modulating cascaded groups can be generally perpendicular to each other.

In accordance with an embodiment of the present invention the modulation system 401 is part of a radiotherapy system that includes a radiation source 408, such as but not limited to, a LINAC, operable to produce radiation beam 402 towards a target 409, an orientation changer 410 (e.g., turntable, gantry, etc.) operable to change a relative position of radiation beam 402 with respect to target 409 and a beam modifier 413 (e.g., a collimator) operable to change during irradiation an aperture of radiation beam 402. The processor 406 is operative to determine operating times or motion speed for changing the respective positions of the modulators between the in-beam and out-of-beam positions. Radiation beam 402 can be shaped as a pencil-beam, fan-beam, cone-beam and other shapes.

Figure 2A:
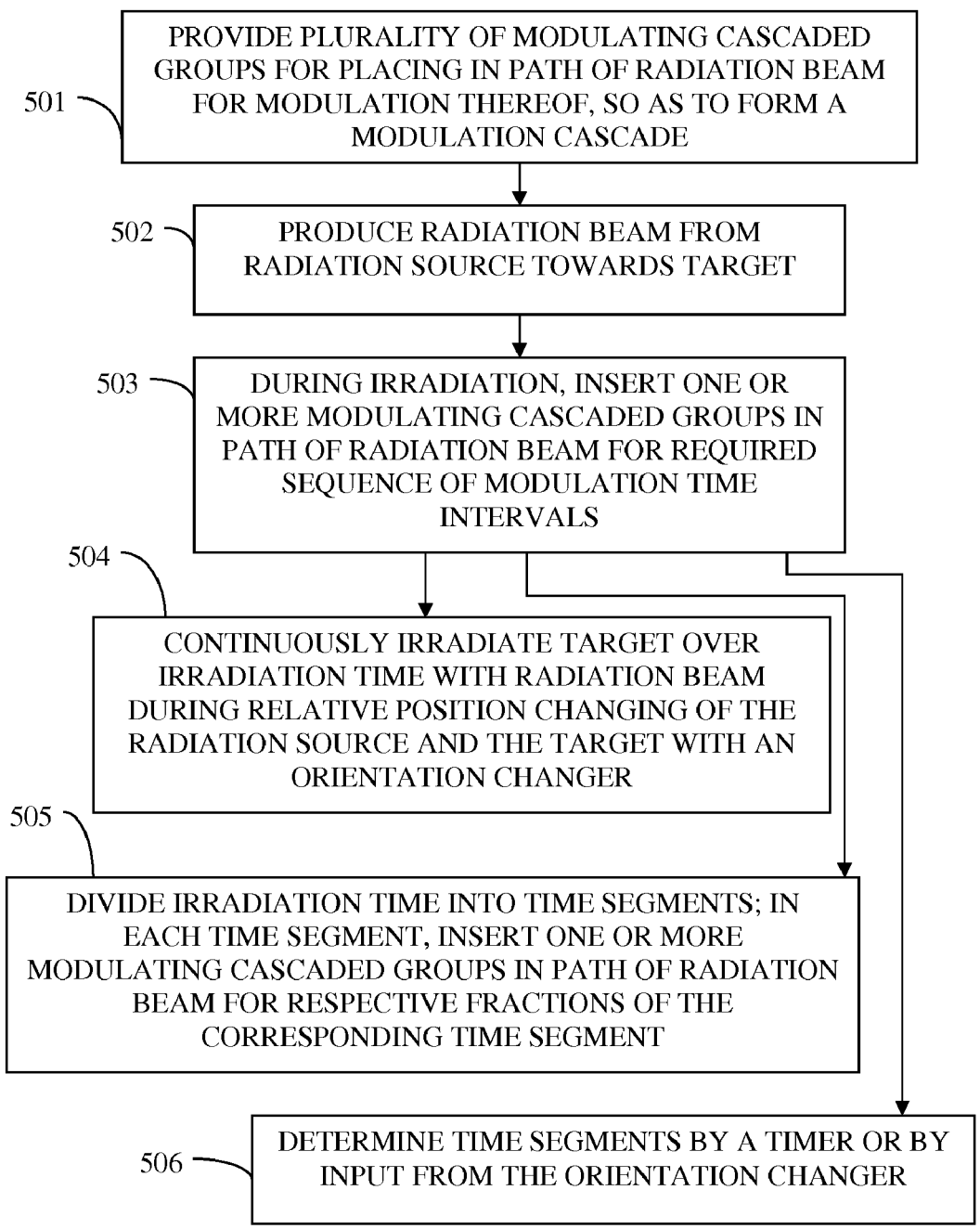
FIGS. 2A-2B form a simplified block diagram of a method for performing radiotherapy with the system of FIG. 1, in accordance with an embodiment of the present invention.
Figure 2B:
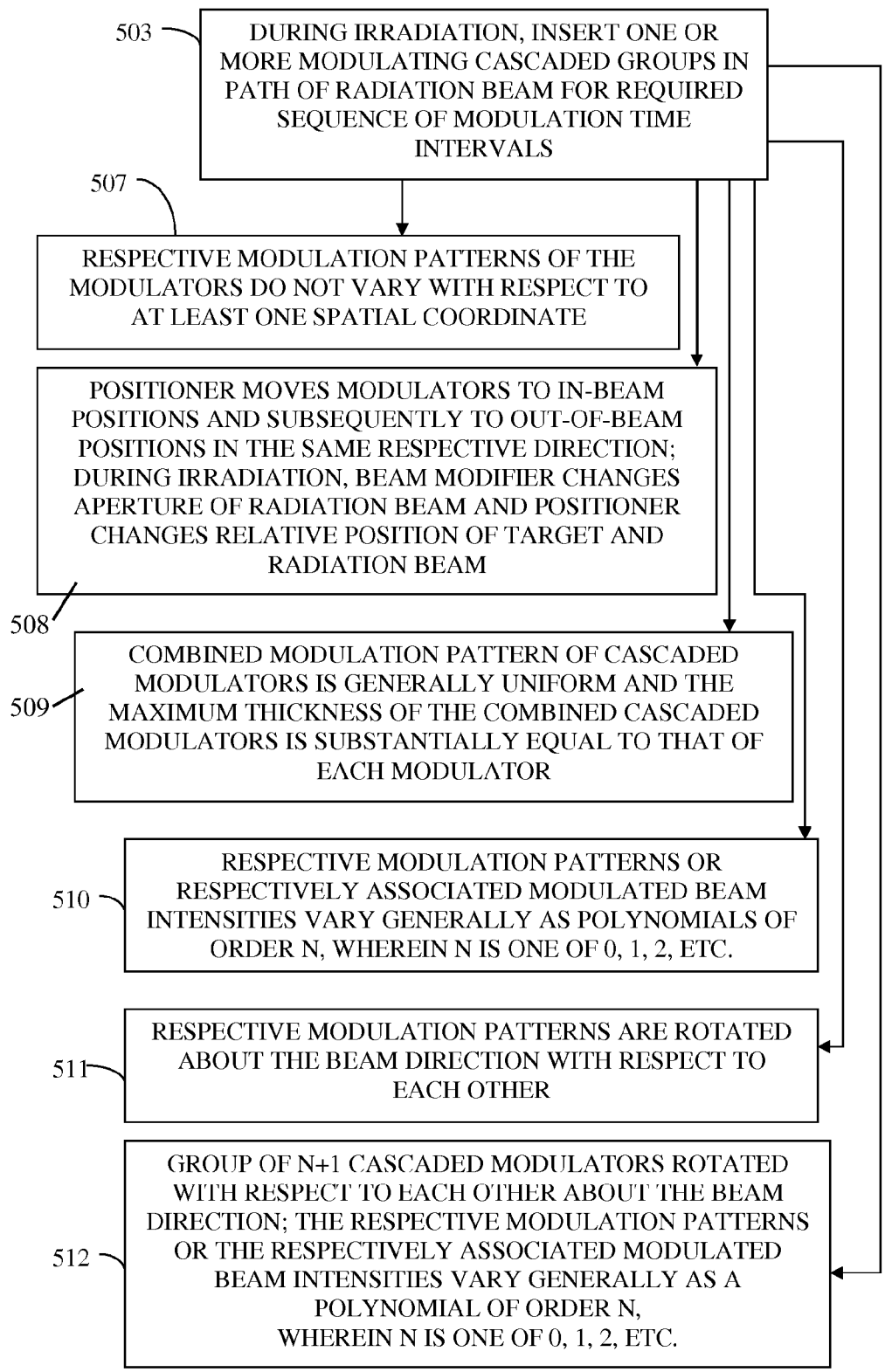

Reference is now made to FIGS. 2A-2B, which illustrates a method for performing radiotherapy with the system of FIG. 1, in accordance with an embodiment of the present invention. A plurality of (e.g., first and second) modulating cascaded groups are provided for placing in the path of the radiation beam for modulation thereof, so as to form a modulation cascade (step 501), as in FIG. 1. The radiation beam is produced from the radiation source towards the target (step 502), as in FIG. 1. During irradiation, one or more of the modulating cascaded groups are inserted in the path of the radiation beam for a required sequence of modulation time intervals (step 503).

In accordance with an embodiment of the present invention the method includes continuously irradiating the target over an irradiation time with the radiation beam during relative position changing of the radiation source and the target with an orientation changer (step 504).

In accordance with another embodiment of the present invention the method includes dividing the irradiation time into time segments, wherein in each time segment, at least one of the first and second modulating cascaded groups is inserted in the path of the radiation beam for respective fractions of the corresponding time segment (step 505).

In accordance with another embodiment of the present invention the method includes determining the time segments by a timer or by input from the orientation changer (step 506).

In accordance with an embodiment of the present invention the modulators are configured such that their respective modulation patterns do not vary with respect to at least one spatial coordinate (step 507).

In accordance with an embodiment of the present invention the positioner is operable to move the modulators to in-beam positions and subsequently to out-of-beam positions in the same respective direction. During irradiation, the beam modifier is operable to change an aperture of the radiation beam and the positioner is operative to change a relative position of the target and the radiation beam (step 508).

In accordance with an embodiment of the present invention the modulation system includes cascaded modulators such that the combined modulation pattern of the cascaded modulators is generally uniform and the maximum thickness of the combined cascaded modulators is substantially equal to that of each modulator (step 509).

In accordance with an embodiment of the present invention the modulation system includes cascaded modulators configured such that their respective modulation patterns or the respectively associated modulated beam intensities vary generally as polynomials of order N, wherein N is one of 0, 1, 2, etc. (step 510).

In accordance with an embodiment of the present invention the modulation system includes cascaded modulators whose respective modulation patterns are rotated about the beam direction with respect to each other (step 511).

In accordance with an embodiment of the present invention the modulation system includes a group of N+1 cascaded modulators rotated with respect to each other about the beam direction, wherein the N+1 cascaded modulators are configured such that their respective modulation patterns or the respectively associated modulated beam intensities vary generally as a polynomial of order N, wherein N is one of 0, 1, 2, etc. (step 512).

Figure 3:
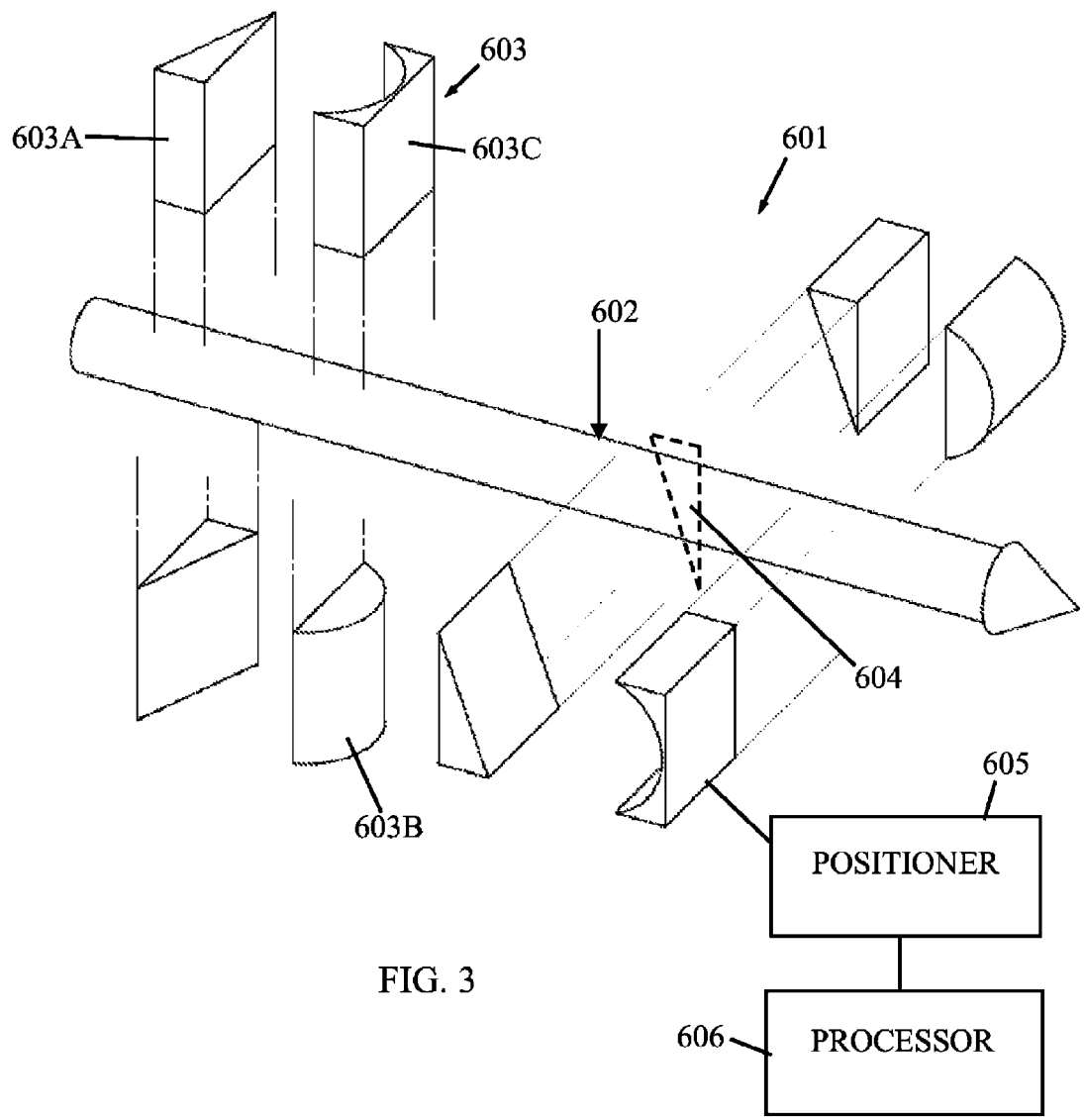
FIG. 3 is a simplified illustration of a modulation system for modulating a radiation beam, constructed and operative in accordance with another embodiment of the present invention.

Reference is now made to FIG. 3, which illustrates a modulation system 601 for modulating a radiation beam 602 (emitted by a radiation source not shown in FIG. 3, but could be the source 408 as above), constructed and operative in accordance with another embodiment of the present invention.

The modulation system 601 includes a plurality of modulators 603, which may be constructed of different shapes (and sizes), such as but not limited to, a triangular wedge 603A, a convex half-cylinder 603B, and a rectangular block 603C with a concave half-cylinder groove formed therein. The modulators 603 are all individually or collectively placeable in the path of radiation beam 602, in any linear or rotational direction, for modulation thereof, as described above. FIG. 3 shows the modulators 603 retracted to out-of-beam positions (i.e., the beam is not attenuated). One of the modulators is shown in the path of the beam (indicated by dashed lines 604); in this position the beam is blocked (attenuated, that is, modulated).

A positioner 605 (e.g., step motor, linear actuator, etc.) is operative to insert one or more of the modulators 603 in the path of radiation beam 602 for a required sequence of modulation time intervals. A processor 606 is operative to determine the required sequence of modulation time intervals and communicates with positioner 605 to control the operation of positioner 605.

In the embodiment of FIG. 3, although not shown in FIG. 3, the orientation changer 410 can be used as described above to change the relative position of the radiation beam (e.g., beam 402) with respect to the target (e.g., target 409), and the beam modifier 413 can change the aperture of the beam during irradiation.

The method described with reference to FIGS. 2A-2B can also be implemented for the embodiment of FIG. 3.

The scope of the present invention includes both combinations and subcombinations of the features described hereinabove as well as modifications and variations thereof which would occur to a person of skill in the art upon reading the foregoing description and which are not in the prior art.

What is claimed is:

1. A modulation system for modulating a radiation beam toward a target, comprising:
    a plurality of cascaded modulators;
    a positioner operable to change positions of each of said modulators between in-beam and out-of-beam positions, wherein in said in-beam position said modulator is in a path of a radiation beam for at least a majority of a total cross-section of said beam and in said out-beam position said modulator is not in the path of the radiation beam; and
    a processor in communication with a beam modifier and with said positioner operative to determine operating times or motion speed for changing the respective positions of said modulators between said in-beam and out-of-beam positions, wherein said beam modifier is operable to change during irradiation an aperture of said radiation beam and said positioner is operative to change during irradiation a relative position of said target and said radiation beam.

2. The modulation system according to claim 1, wherein said modulators are configured such that their respective modulation patterns do not vary with respect to at least one spatial coordinate.

3. The modulation system according to claim 1, wherein said positioner is operable to move said modulators to the in-beam positions and subsequently to the out-of-beam positions in the same respective direction.

4. The modulation system according to claim 1, wherein a combined modulation pattern of said cascaded modulators is generally uniform and a maximum thickness of the combined cascaded modulators is substantially equal to that of each said modulator.

5. The modulation system according to claim 1, wherein said cascaded modulators are configured such that their respective modulation patterns or their respectively associated modulated beam intensities vary generally as polynomials of order N, wherein N is one of 0, 1, 2, etc.

6. The modulation system according to claim 1, wherein said cascaded modulators are configured such that their respective modulation patterns are rotated about the beam direction with respect to each other.

7. The modulation system according to claim 1, wherein said cascaded modulators comprise a group of N+1 cascaded modulators rotated with respect to each other about the beam direction, wherein the N+1 cascaded modulators are configured such that their respective modulation patterns or their respectively associated modulated beam intensities vary generally as a polynomial of order N, wherein N is one of 0, 1, 2, etc.

8. The modulation system according to claim 1, wherein said positioner is operable to change the position of each said modulator in less than 100 msec.

9. A radiotherapy system comprising:
    the modulation system of claim 1;
    a radiation source operable to produce a radiation beam towards a target;
    a collimator; and
    an orientation changer operable to change a relative position of the radiation source with respect to the target.

10. A method for performing radiotherapy comprising:
    producing a radiation beam from a radiation source toward a target; and inserting combinations of the cascaded modulators of the modulation system of claim 1 in the path of the radiation beam for corresponding time intervals.

11. The method according to claim 10, comprising relating the corresponding time intervals to outputs of at least one of a timer, a radiation sensor and the orientation changer.

12. The method according to claim 10, comprising continuously irradiating the target over an irradiation time with the radiation beam modulated by the modulation system, wherein the relative position of the radiation source with respect to the target during irradiation is fixed.

13. The method according to claim 10, comprising continuously irradiating the target over an irradiation time with the radiation beam modulated by the modulation system, wherein the relative position of the radiation source with respect to the target during irradiation is changing.

* * * * *